United States Patent [19]
Bonati et al.

[11] Patent Number: 5,290,279
[45] Date of Patent: Mar. 1, 1994

[54] ARTHROSCOPIC TOOL COMBINING FIVE FUNCTIONS IN ONE

[75] Inventors: Alfred O. Bonati, New Port Richey; Philip J. Ware, Spring Hill, both of Fla.

[73] Assignee: Meditron Devices, Inc., Hackensack, N.J.

[21] Appl. No.: 62,506

[22] Filed: May 17, 1993

Related U.S. Application Data

[63] Continuation-in-part of Ser. No. 810,622, Dec. 19, 1991, abandoned.

[51] Int. Cl.$^5$ .............................................. A61B 1/06
[52] U.S. Cl. ........................................ 606/15; 128/4; 606/7; 606/16
[58] Field of Search ............... 604/4, 6; 606/15, 13, 606/14, 16, 2, 3, 7, 10, 11, 12

[56] References Cited

U.S. PATENT DOCUMENTS

| | | | |
|---|---|---|---|
| 2,992,956 | 7/1961 | Bazinet, Jr. | 385/146 |
| 4,587,972 | 5/1986 | Morantte, Jr. | 606/15 X |
| 4,832,024 | 5/1989 | Boussignac et al. | 606/15 X |
| 4,848,336 | 7/1989 | Fox et al. | 606/7 |
| 4,875,897 | 10/1989 | Lee | 606/15 X |
| 4,911,148 | 3/1990 | Sosnowski et al. | 128/4 |
| 4,928,695 | 5/1990 | Goldman et al. | 606/15 X |
| 5,026,367 | 6/1991 | Leckrone et al. | 606/7 |
| 5,083,549 | 1/1992 | Cho et al. | 128/4 |

Primary Examiner—Peter A. Aschenbrenner
Attorney, Agent, or Firm—Joseph C. Mason, Jr.; Ronald E. Smith

[57] ABSTRACT

A multi-function arthroscope has a laser channel, an irrigation tube, a suction tube, a rod lens, and optical fibers housed within a tubular casing. The operation site is illuminated by the optical fibers, and the physician views the illuminated site through the rod lens, performs laser surgery with laser radiation propagated by the laser channel, irrigates the site and cleans the rod lens with saline solution through the irrigation tube, and vacuums the debris with the suction tube, all in a single insertion of the arthroscope through a dilator tube. The respective distal ends of the optical fibers, rod lens, laser channel, irrigation tube, and the suction tube are positioned in different planes so that the suction tube extends in a distal direction further than the laser channel, the laser channel extends further than the irrigation tube, and the irrigation tube extends further than the rod lens. Connector members join the laser channel, the irrigation tube, the suction tube, and the optical fibers and rod lens to an external source of coherent light, an external source of saline solution under positive pressure, an external source of negative pressure, and an external source of incoherent light, respectively.

25 Claims, 2 Drawing Sheets

ARTHROSCOPIC TOOL COMBINING FIVE FUNCTIONS IN ONE

This is a continuation-in-part of copending application(s) Ser. No. 07/810,622 filed on Dec. 19, 1991 abandoned.

BACKGROUND OF THE INVENTION

1. Field of the Invention

This invention relates, generally, to surgical instruments. More particularly, it relates to a multi-function arthroscope.

2. Description of the Prior Art

Arthroscopic surgery is usually performed under illumination provided by light transmitted through optical fibers. A laser may be used in some surgical procedures to vaporize tissue or other material. The operation site, typically, is irrigated with a saline solution to place the debris into suspension and a vacuum means is employed to remove the saline and debris. A rod lens enables the physician to see the operation site.

The prior art teaches that different instruments must be employed to perform these tasks. A dilator tube is first inserted through the initial incision; a plurality of instruments, each dedicated to a different task, is then sequentially inserted into and withdrawn from the dilator tube as the operation progresses. Such use of a dilator tube avoids the trauma that would be caused by repeated insertion and withdrawal of instruments through an unprotected incision.

However, repeated switching of tools and repeated entries and exits through the dilator tube consumes time and increases the chances that a mistake might be made at some step of the procedure. Accordingly, there is a need for a simplified procedure. Ideally, an entire operation could be performed using only a single incision and a single entry and exit through a dilator tube, but the prior art contains inadequate information to indicate to those of ordinary skill in this art as to how such an ideal situation could be achieved.

U.S. Pat. No. 5,083,549 to Cho et. al. shows a multi-function endoscopes, but endoscopes have no utility in cervical or lumbar applications. More importantly, the Cho device does not teach or suggest how to position the multiple elements in a manner where such multiple elements would have utility in an arthroscope.

SUMMARY OF THE INVENTION

The present invention includes a tool that combines a total of five functions into a single instrument so that an entire arthroscopic procedure can be performed with a single incision and a single insertion and withdrawal of said instrument through a dilator tube.

In a first embodiment, four tubular members are positioned in closely spaced, parallel relation to one another and optical fibers fill the interstitial spaces between them. An epoxy surrounds the optical fibers and a cylindrical metal casing ensleeves all of said parts. Each of the four tubes and said optical fibers is dedicated to a particular function. Significantly, the respective distal ends of each of the four tubes and optical fibers is specifically positioned relative to the respective distal ends of the other elements so that the function of each element is efficiently performed.

The first element is the laser channel; it delivers laser radiation to the surgical site and consists of a flexible glass fiber core covered by a cylindrical layer of rubber, synthetic rubber, or other suitable elastomer, and the elastomeric material is similarly covered by a cylindrical layer of a metallic substance. The glass fiber core is the medium that propagates the laser radiation.

A second element, called herein the irrigation tube, delivers saline solution to the site for irrigation purposes and a third element, herein called the suction tube, has a proximal end connected to a source of negative pressure to vacuum the saline solution and debris floated thereby.

The fourth element is the rod lens; it has mirrored cylindrical interior side walls and is aligned with the lens of the arthroscope. Other rod lens designs and other devices that enable a surgeon to view the surgical site are also within the scope of this invention. Light that is delivered to the surgical site is reflected to the surgeon's eyes in substantially undiminished intensity due to the optical qualities of the rod lens or other viewing device.

All four tubular elements are positioned within a stainless steel casing in parallel alignment with one another and a plurality of optical fibers fill the spaces between them and the stainless steel casing as aforesaid. A cylindrical layer of epoxy or other suitable adhesive encases the bundle of optical fibers and tubes and adheres the bundle to the stainless steel casing.

The stainless steel casing has an outside diameter less than the inside diameter of the dilator tube and is thus easily introduced through said dilator tube when a surgical procedure is under way.

The novel arthroscope further includes a base member near the proximal end thereof. The base member houses, at least in part, the respective proximal ends of the rod lens, the laser channel, the irrigation tube, the suction tube, the optical fibers, and the casing. The base member has a predetermined width so that the respective proximal ends of said five elements are spaced apart from one another before entering the stainless steel casing that houses them.

The width of the base member provides ample space for the connection thereto of multiple connection members that provide an interface means between the elements of the instrument and parts external to the instrument. More particularly, a first connector is mounted to a trailing edge of the base member and detachably interconnects the proximal end of the laser channel with an external source of laser radiation. A second connector is similarly mounted to a trailing edge of the base member and detachably interconnects the proximal end of the irrigation tube to an external source of saline solution under positive pressure. A third connector, also mounted to a trailing edge of the base member, detachably interconnects the proximal end of the suction tube to an external source of negative pressure. A fourth connector is disposed normal to the base member; it interconnects the respective proximal ends of the rod lens and the bundle of optical fibers to a source of light. A prism within the instrument bends the light as required.

The first, second, and third connectors are angularly disposed with respect to the longitudinal axis of the stainless steel casing that houses the bundle of tubes and the optical fibers. Accordingly, the respective proximal ends of the first, second, and third tubular members are bent slightly as required within the base member so that they are parallel to one another within said stainless steel casing.

The distal end of the irrigation tube extends slightly beyond the distal end of the rod lens so that irrigation fluid flowing out of the irrigation tube will flow across the face of the rod lens and clean it.

Similarly, the distal end of the laser channel extends beyond the distal end of the rod lens so that smoke created by the laser does not cloud the distal end of the rod lens. The distal end of the suction tube extends beyond the distal end of the laser channel so that the laser does not waste its energy on heating the irrigation fluid, i.e., the distal or leading end of the suction tube extends beyond the distal or leading end of the laser channel to insure that the irrigation fluid is suitably vacuumed to enhance the performance of the laser channel.

In a second embodiment, the optical fibers are eliminated and a self-illuminating rod lens is used. This construction eliminates the epoxy and the tubular casing as well.

Thus it should be clear that the primary object of this invention is to advance the art of arthroscopes in a pioneering, revolutionary way.

A more specific object is to provide the first arthroscope, anywhere in the world, that performs five functions.

Another important object is to combine the functions of laser application, irrigation, vacuuming, viewing, and illumination in a single instrument.

These and many other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
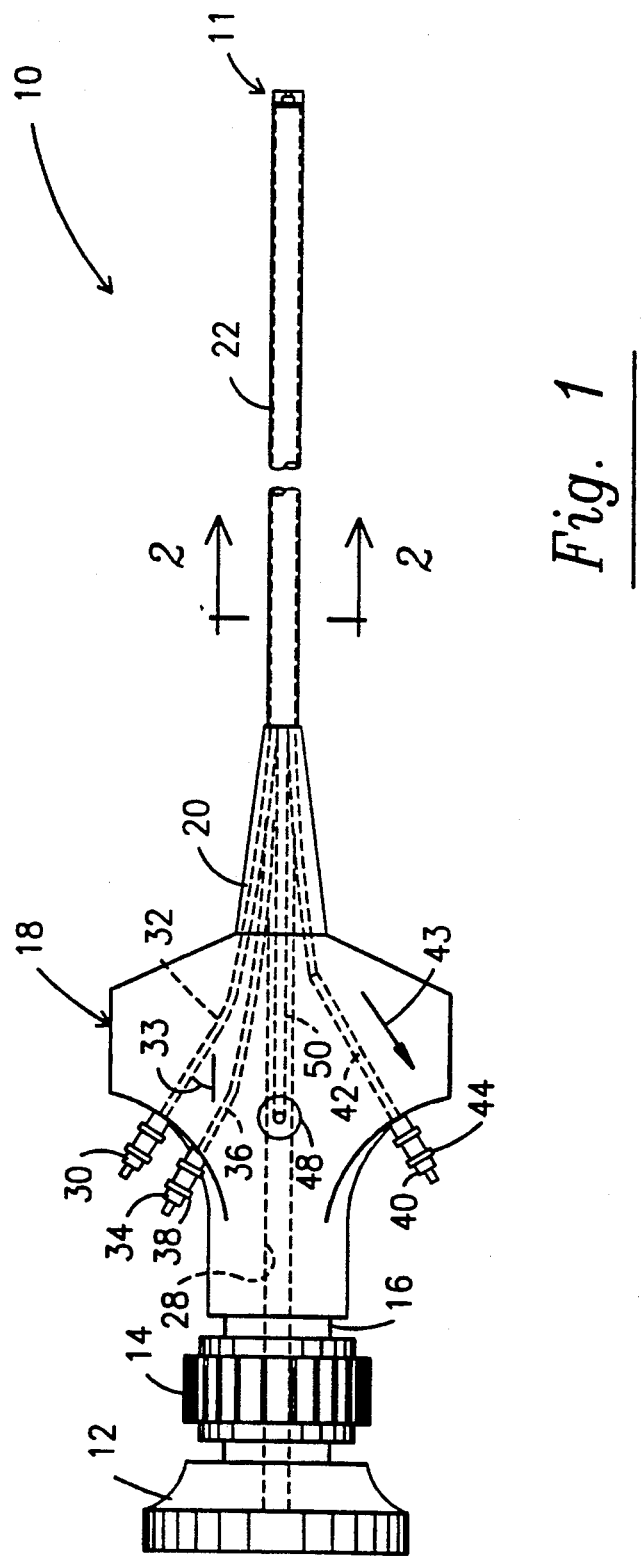
FIG. 1 is a top plan view of the novel arthroscope.

Referring now to FIG. 1, it will there be seen that the novel arthroscope is denoted as a whole by the reference numeral 10; it has a distal end 11 that is positioned at the site of the surgical procedure when instrument 10 is in use.

Arthroscope 10 further includes lens 12, at the proximal end of the device, a knurled lens adjustment means 14 that focuses the lens when rotated, a cylinder 16 that carries the adjustment means and the lens, a base member 18 that is also mounted to cylinder 16, a tapered boss means 20 mounted to the distal end of base 18, and a tubular stainless steel casing 22 having a proximal end held by said boss means.

First connector means 30 (FIG. 1) is mounted at a trailing edge of base 18 in coplanar relation thereto and detachably connects an external source of laser radiation, not shown, to laser channel 32 that extends from connector 30 to the distal end 11 of the novel arthroscope.

Base 18 is preferably of hollow construction and channel 32 is preferably a rod-like member. More particularly, laser channel 32 has a glass fiber core that is wrapped by a suitable, cylindrically-shaped elastomeric material to give it flexibility and said elastomeric material is similarly encased in a suitable metallic sheath. Angle 33 is preferably between 22-35 degrees.

Second connector means 34 is also mounted to a trailing edge of base 18 in coplanar relation thereto and provides fluid communication between an external, positive pressure source of irrigating fluid, such as a suitable saline solution, not shown, and the irrigation tube 36 that carries said solution to said distal end 11. A suitable valve means 38 enables the physician to control the rate of flow of said solution through tubular member 36. A first purpose of the irrigation is to float surgical debris to thereby facilitate removal of said debris from the site of the surgical procedure; a second purpose is to clean the face of the rod lens 46.

An external source of negative pressure is detachably coupled to the trailing end of base 18 of arthroscope 10 by third connector means 40. Suction tube 42 extends from said third connector to the distal end 11 of the arthroscope and carries the irrigating solution and debris to an external collection tank, not shown. The physician controls the amount of suction and hence the vacuum rate by manipulating control valve 44.

A rod lens 46 (FIG. 2) of linear configuration is the fourth of the five elements disposed within the casing; it extends from lens 12 to the distal end 11 of the arthroscope 10. Rod lens 46 is of tubular construction and has mirrored cylindrical side walls to propagate light in substantially undiminished intensity from said distal end 11 to said lens 12 when the site of the surgical procedure is illuminated.

Fourth connector means 48 (FIG. 1) is mounted orthogonally with respect to base member 18; it provides means for detachably securing a first bundle of optical fibers, not shown, thereto. Light from said first bundle enters rod lens 46 through a prism, not shown. Reference numeral 50 represents a second bundle of optical fibers that extends from a point near the internal end of connector 48 to the distal end 11 of the arthroscope. Said prism also transmits light from the first bundle to the second. As best understood in connection with FIG. 2, the second bundle 50 of optical fibers includes a large plurality of individual optical fibers that are interspersed around and between laser channel 32, irrigation tube 36, suction tube 42, and rod lens 46; said fibers illuminate the surgical site.

Epoxy 52 or other suitable adhesive is employed to encase the second bundle of optical fibers about its longitudinal extent, and the resulting cylindrical structure of optical fibers wrapped in epoxy is ensleeved by stainless steel casing 22.

Figure 2:
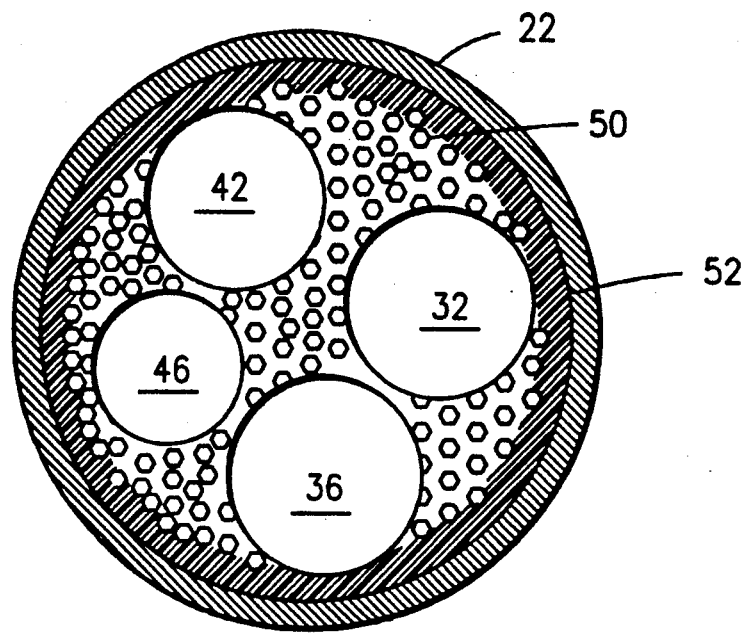
FIG. 2 is a transverse sectional view taken along lie 2—2 in FIG. 1.

The particular positioning of each of the tubular members relative to one another as shown in FIG. 2 is not critical to the invention.

Figure 3:
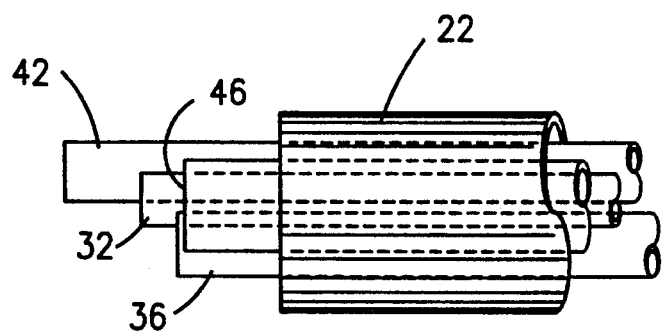
FIG. 3 is an enlarged plan view of the respective distal ends of the separate elements housed within the arthroscope.

However, the positions of the respective distal ends of the optical fibers, irrigation tube, rod lens, laser channel, and suction tube are important. As shown in FIG. 3, (epoxy 52 and optical fibers 50 are deleted from FIG. 3 to simplify it) the distal end of irrigation tube 36 leads the distal end of the rod lens 46 by a small amount. In a preferred embodiment, the distance is about one-half mm. This specific positioning of irrigation tube 36 with respect to rod lens 46 enables cleaning of the leading face of the rod lens with irrigation fluid.

Moreover, the distal end of laser channel 32 leads the face of rod lens 46 by about two mm. This distance sufficiently spaces the rod lens from the smoke produced by the laser channel.

The distal end of suction tube 42 leads the distal end of the rod lens by about five mm as depicted to ensure that all irrigation fluid on the distal side of the laser channel will be vacuumed out of the way so that the laser can efficiently perform its function.

Lastly, the distal end of the optical fibers 50 is substantially coincident with, or trails slightly, i.e., by one-half mm or so, the distal end of the rod lens 46. The exact positioning is mathematically determined by factors such as the length of said optical fibers, their diameter, the focal distance, and the like.

Thus, the respective distal ends of the five elements within casing 22 are staggered with respect to one another and this staggering enables all four individual tools to perform their respective functions in an optimal manner.

This invention is clearly new and useful. Moreover, it was not obvious to those of ordinary skill in this art at the time it was made, in view of the prior art when considered as a whole in accordance with the requirements of law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An arthroscope, comprising:
   a tubular casing having a proximal end and a distal free end;
   a laser channel means having a distal end disposed within said tubular casing, said laser channel means being disposed in light transmitting relation to a source of laser radiation external to said arthroscope;
   an irrigation tube having a distal end disposed within said tubular casing, said irrigation tube being disposed in fluid communication with a source of liquid fluid under positive pressure external to said arthroscope;
   a suction tube having a distal end disposed within said tubular casing, said suction tube having a proximal and disposed in fluid communication with a source of negative pressure external to said tool;
   a lens for facilitating viewing of an operation site disposed at the proximal end of the tubular casing;
   a rod lens means disposed within said tubular casing, said rod lens means being disposed in alignment with said lens;
   a plurality of optical fibers disposed within said tubular casing, said optical fibers occupying interstitial space in said tubular casing between said laser channel, said irrigation tube, said suction tube, and said rod lens, said optical fibers being in light transmitting relation with a source of light external to said tool;
   said irrigation tube distal end disposed, by a predetermined distance, in leading relation to said rod lens distal end so that irrigation fluid from said irrigation tube cleans said rod lens;
   said laser channel disposed, by a predetermined distance, in leading relation to the distal end of said rod lens so that smoke produced by said laser channel does not impair the physician's view through said rod lens;
   said suction channel disposed, by a predetermined distance, in leading relation to the distal end of said laser channel so that irrigation fluid is vacuumed by said suction tube and thus does not interfere with operation of said laser channel;
   whereby said arthroscope has utility in arthroscopic surgery when a physician views the operation site through said lens and said rod lens, illuminates the site through said optical fibers, performs a surgical operation with laser radiation transmitted to the site through said laser channel, irrigates the site with liquid fluid transmitted to the site through said irrigation tube, and vacuums the site through said suction tube.

2. The arthroscope of claim 1, further comprising a base means having a predetermined width, said base means at least in part receiving said laser channel, said irrigation tube, said suction tube, said rod lens, and said optical fibers.

3. The arthroscope of claim 2, further comprising a first connector means for detachably connecting a source of laser radiation external to said arthroscope to said laser channel, said first connector means being mounted to said base means.

4. The arthroscope of claim 3, further comprising a second connector means for detachably securing an external source of an irrigating solution under positive pressure to said irrigation tube, said second connector means being mounted to said base means.

5. The arthroscope of claim 4, further comprising an irrigation control valve, formed in said second connector means, for controlling the flow rate of liquid fluid introduced to the operation site through said irrigation tube.

6. The arthroscope of claim 5, further comprising a third connector means for detachably securing an external source of negative pressure to said suction tube, said third connector means being mounted to said base means.

7. The arthroscope of claim 6, further comprising a suction control valve, formed in said third connector means, for controlling the flow rate of liquid fluid from said operation site through said suction tube.

8. The arthroscope of claim 7, wherein said rod lens is disposed in parallel relation to said tubular casing along the entire extent of said tubular casing.

9. The arthroscope of claim 8, wherein said laser channel has a proximal end that is disposed at a predetermined angle with respect to said base means.

10. The arthroscope of claim 9, wherein said irrigation tube has a proximal end disposed at a predetermined angle with respect to said base means.

11. The arthroscope of claim 10, wherein said suction tube has a proximal end disposed at a predetermined angle with respect to said base means.

12. The arthroscope of claim 11, further comprising a fourth connector means for detachably connecting an external source of light to said rod lens and to said optical fibers, said fourth connector means being mounted to said base means.

13. The arthroscope of claim 12, wherein said fourth connector means is disposed normal to a preselected surface of said base member.

14. The arthroscope of claim 13, further comprising a prism disposed in operative relation to said fourth connector means, said prism being operative to transmit light from said external source of light to said rod lens and to said optical fibers.

15. The arthroscope of claim 14, further comprising adjustment means for adjusting the focus of said lens.

16. The arthroscope of claim 15, wherein said optical fibers are encased within an adhesive means.

17. The arthroscope of claim 16, wherein said adhesive means forms a cylindrical layer around said optical fibers and wherein said adhesive means further adheres said optical fibers to said tubular casing.

18. The arthroscope of claim 17, wherein said tubular casing is a stainless steel tube.

19. The arthroscope of claim 1, wherein the predetermined distance by which said irrigation tube leads said rod lens distal end is about one-half mm.

20. The arthroscope of claim 1, wherein the predetermined distance by which said distal end of said laser channel leads said distal end of said rod lens is about two mm.

21. The arthroscope of claim 1, wherein the predetermined distance by which said suction tube distal end leads said rod lens distal end is about five mm.

22. An arthroscope, comprising:
a tubular casing;
a laser channel disposed within said tubular casing;
an irrigation tube disposed within said tubular casing;
a suction tube disposed within said tubular casing;
a rod lens disposed within said tubular casing;
said laser channel, said irrigation tube, said suction tube, and said rod lens being disposed in substantially parallel relation to one another;
a plurality of optical fibers disposed between and around said laser channel, said irrigation tube, said suction tube, and said rod lens;
a cylindrical layer of adhesive disposed around said optical fibers;
said adhesive securing said optical fibers to said tubular casing;
a base means mounted on said tubular casing;
a first connector means, mounted on said base means, for detachably connecting a proximal end of said laser channel to an external source of laser radiation;
a second connector means, mounted on said base means, for detachably connecting a proximal end of said irrigation tube to an external source of irrigating liquid fluid under positive pressure;
a third connector means, mounted on said base means, for detachably connecting a proximal end of said suction tube to an external source of negative pressure;
a fourth connector means, mounted on said base. means, for connecting respective proximal ends of said rod lens and said optical fibers to an external source of electromagnetic radiation;
an adjustable lens means disposed in light transmitting relation to said rod lens;
said irrigation tube distal end disposed, by a predetermined distance, in leading relation to said rod lens distal end so that irrigation fluid from said irrigation tube cleans said rod lens;
said laser channel disposed, by a predetermined distance, in leading relation to the distal end of said rod lens so that smoke produced by said laser channel does not impair the physician's view through said rod lens;
said suction channel disposed, by a predetermined distance, in leading relation to the distal end of said laser channel so that irrigation fluid is vacuumed by said suction tube and thus does not interfere with operation of said laser channel;
whereby said arthroscope performs multiple functions and is employed to perform multiple surgical procedures with a single insertion through a single incision.

23. The arthroscope of claim 22, wherein the predetermined distance by which said irrigation tube leads said rod lens distal end is about one-half mm.

24. The arthroscope of claim 22, wherein the predetermined distance by which said distal end of said laser channel leads said distal end of said rod lens is about two mm.

25. The arthroscope of claim 22, wherein the predetermined distance by which said suction tube distal end leads said rod lens distal end is about five mm.

* * * * *